United States Patent [19]

Dowling et al.

[11] 4,423,267
[45] Dec. 27, 1983

[54] SUPPORTED FERRIC SULFATE AND COBALT SULFATE CATALYSTS FOR THE OLIGOMERIZATION OF OLEFINS

[75] Inventors: Robin M. Dowling, Tonkawa; David P. Higley, Ponca City, both of Okla.

[73] Assignee: Conoco Inc., Ponca City, Okla.

[21] Appl. No.: 383,412

[22] Filed: Jun. 1, 1982

[51] Int. Cl.$^3$ .................................................. C07C 2/02
[52] U.S. Cl. ................................... 585/531; 585/526
[58] Field of Search ................................ 585/526, 531

[56] References Cited

U.S. PATENT DOCUMENTS

| | | | |
|---|---|---|---|
| 2,082,454 | 6/1937 | Kuentzel | 585/517 |
| 2,224,071 | 12/1940 | Wassermann | 526/118 |
| 2,732,329 | 3/1956 | Doumani | 208/107 |
| 2,794,842 | 6/1957 | Hogan et al. | 585/526 |
| 3,132,122 | 5/1964 | Dunay et al. | 526/172 |
| 3,156,680 | 11/1964 | Dunay et al. | 526/172 |
| 3,239,576 | 3/1966 | Appleby et al. | 585/255 |
| 3,271,474 | 9/1966 | Engelbrecht et al. | 585/531 |
| 3,959,400 | 5/1976 | Lucki | 585/515 |
| 3,966,640 | 6/1976 | Katz et al. | 252/440 |
| 4,214,112 | 7/1980 | Mandai et al. | 585/532 |

*Primary Examiner*—Curtis R. Davis
*Attorney, Agent, or Firm*—Robin M. Davis

[57] ABSTRACT

Iron sulfate supported on alumina or silica alumina and cobalt sulfate supported on alumina are catalysts used for olefin oligomerization. These new catalysts allow olefin oligomerizations to be carried out at lower temperatures than many other known catalysts. The reaction is normally carried out under sufficient pressure to keep the olefin present as a liquid. In addition, the catalysts provide excellent selectivity for the formation of lower olefins and require no water to maintain activity, thereby leading to increased productivity by avoiding problems of polymerization, coking and reactor plugging.

12 Claims, No Drawings

SUPPORTED FERRIC SULFATE AND COBALT SULFATE CATALYSTS FOR THE OLIGOMERIZATION OF OLEFINS

This invention relates to the oligomerization of olefins. It should be noted that the word "olefin" is herein interpreted as being a class of unsaturated aliphatic hydrocarbons having one or more double bonds. The catalysts useful in this regard comprise ferric sulfate supported on alumina or silica-alumina, and cobalt sulfate supported on alumina. These catalysts are especially useful for the dimerization of butenes, the oligomerization of propene, or the codimerization of butenes and propene to form highly-branched olefinic products.

Catalysts used to oligomerize olefins to form highly-branched products are well known in the art, and are used extensively in the petroleum industry for the principal purpose of converting light olefins to high-octane gasoline blending stock.

Supported nickel sulfate is known as a catalyst (U.S. Pat. No. 2,732,329) and is known to be useful for the polymerization and dimerization of olefins (U.S. Pat. Nos. 2,794,842 and 3,959,400). Since nickel is in the same chemical family as iron and cobalt, the oligomerization chemistry of this system is discussed and compared extensively with a given comparison example.

Ferric sulfate has been useful in a few catalytic systems used for polymerization of certain monomers. Specifically, ferric sulfate is reported as capable of use in a nonsupported fashion for the polymerization of vinyl ethers and also for the polymerization of nitrile monomers in U.S. Pat. Nos. 3,156,680 and 3,132,122 respectively. The capacity in which ferric sulfate is employed in these two systems, however, is not at all indicative of any ability on the part of ferric sulfate to oligomerize olefins or, more generally, how supported ferric sulfate or cobalt sulfate would act in an oligomerization system. Moreover, the process of polymerization not only is distinct from oligomerization, but the tendency to polymerize is an undesirable trait in olefin oligomerizations. If, for example, olefins are polymerized by a specific catalyst instead of being oligomerized, there is very little selectivity to the lower olefin products such as dimers or trimers. Thus, the tendency to polymerize as opposed to oligomerize is a disadvantage for any catalyst used in an oligomerization system. In view of the prior art it would be expected that a ferric sulfate catalyst either would be incapable of use in an oligomerization system or would have the disadvantage of polymerizing olefin into a higher undesired olefinic product. Contrary to these expectations, both the supported ferric sulfate and cobalt sulfate catalytic systems are selective to the lower olefin oligomers avoiding polymerization as a problem.

U.S. Pat. No. 2,224,071 teaches "the catalytic reaction of hydrocarbons" using a supported heavy metal sulfide activated by association with sulfate. Ferric sulfide is one of the heavy metal compounds taught which may be used. However, these catalysts require first the preparation of the metal sulfide, which is then activated by exposure to oxygen or sulfate. Higher temperatures are required for this catalytic system, the minimum temperatures specified for "polymerization" being 100° C. It is also apparent that in spite of the higher temperatures used in these catalytic systems that a low activity is obtained resulting in low amounts of product. There is not only a lack of selectivity to specific oligomers such as dimers and trimers, but there is also no selective production of specific structural isomers within any olefin oligomer class.

Catalytic systems that are useable for polymerization of hydrocarbons are taught in U.S. Pat. No. 3,692,697. One of the catalytic combinations disclosed in this patent is a cobalt sulfate with alumina, hydrogen, and a fluoride. Some fluorine content in this catalyst is necessary. This reported tendency to polymerize hydrocarbons instead of oligomerizing them is a disadvantage to a catalyst when lower olefin oligomers such as dimers and trimers are desired. The cobalt sulfate catalyst of the instant invention thus has a unique and desirable property in its ability to selectively produce lower olefinic oligomerized compounds.

Other cobalt catalysts of varying natures have been known in the chemical arts and have been used for a variety of chemical reactions. The following U.S. patents, for example, reflect the use of cobalt or cobalt compounds in combination with a variety of other compounds, combinations, and conditions. U.S. Pat. No. 4,214,112 teaches that certain cobalt compounds including cobalt sulfate are used in combination with an aluminum halide and certain polyhydric alcohol derivatives in a process for preparing olefin oligomer. Not only does this process tend to produce higher olefin oligomers and even polymers, but it also specifies that it is not used for olefins with less than 6 carbon atoms. U.S. Pat. No. 2,082,454 pertains to the conversion of gaseous olefins into liquid hydrocarbons of the gasoline boiling range using a cobalt chloroaluminate catalyst. This process, however, requires much higher temperatures than the instant invention. Moreover, it is apparent from this patent that this cobalt chloro-aluminate catalyst is used with olefin feed which always contains ethylene, which is described as an activator. Finally, this system does not include the production of specific olefin dimers or trimers, nor does it provide for the selective production of specific olefin structural isomers within the olefin dimer class.

U.S. Pat. No. 3,966,640 discloses cobalt sulfates supported on alumina used as a desulfurization catalyst. This catalytic system is used to permit conversion of sulfur dioxides into elemental sulfur. In view of this divergent use to which a cobalt sulfate alumina catalyst is put, it is surprising that the catalytic system in the instant invention delivers such selectivity when used in an olefin oligomerization system.

Even if polymerization itself is avoided, one problem is an oligomerization reaction which is difficult to avoid is the lack of selectivity to lower olefin products such as dimers or trimers. Many times if an oligomerization catalyst does not have the disadvantage of a tendency to polymerize, it will still have the disadvantage of producing higher olefinic product than is desirable. Furthermore, even if a large quantity of lower olefins is produced, it is extremely rare for an oligomerization catalyst to be capable of selectivity among dimer or trimer compounds produced. The catalysts of the instant invention are therefore remarkable in this respect. As may be seen in the examples offered, there is selectivity not only to the lower olefins, but also to certain olefinic compounds within the dimer or trimer class.

Another disadvantage common to catalysts in the field of olefin oligomerization and polymerization is the requirement of water addition to the feed in order to maintain catalyst activity. Where this water addition is required, corrosion problems are incurred. Moreover, the addition of water results in the softening and eventual plugging of catalysts beds. A catalyst of this nature is exemplified in U.S. Pat. No. 3,239,576 which uses an acidic catalyst to form components for supersonic jet fuel. The catalysts of the instant invention avoid these problems by eliminating the necessity of water.

A further disadvantage found among oligomerization catalyts is the requirement of high operating temperatures. This tends to lead to coking and consequent deactivation of the catalyst. Both the supported ferric sulfate and cobalt sulfate catalysts are active in extremely moderate temperature ranges. This allows lower operating temperatures to be used, and prolongs catalyst life.

In carrying out oligomerization reactions it is thus desirable to have a catalyst which is capable of delivering a variety of advantages. In order to avoid corrosion or softening and plugging of the catalyst bed, the activity should require no water addition. The catalyst should be active at moderate temperatures, providing the added benefit of a greater degree of energy conservation. An equally desirable quality for an oligomerization catalyst is that it should be highly selective for the formation of lower oligomers. It is especially desirable to emphasize the production of dimers and/or trimers at the expense of higher oligomers while using a catalyst which is capable of prolonged activity at moderate temperatures. Catalysts capable of operation at moderate temperatures are able to avoid the coking evidenced at the higher temperatures, and due to the selectivity for lower oligomers, such catalysts avoid deactivation by substrate polymerization.

Another unique characteristic and advantage to the catalytic system of the present invention is the selectivity discovered to specific dimer and trimer compounds. Specifically, these ferric and cobalt sulfate catalysts (and their catalytic systems) have the characteristic of producing highly branched lower olefinic product when oligomerizing olefins. The quantities of this highly branched product, are remarkable in that they are produced in a quantitative abundance as compared with the lightly branched or linear structures. The present invention, therefore, offers not only the remarkable characteristic and advantage of extreme selectivity to dimer product or trimer product but also is selective to specific highly branched olefinic compounds. Compounds of this nature have been used extensively in the petroleum industry as high octane gasoline blending stock.

It is therefore an object of the instant invention to provide a combination of a great variety of advantageous qualities which not only are of individual benefit but are of even greater benefit since they can be obtained by choosing a single catalytic system.

The instant invention provides for catalysts useful for oligomerizing olefin mixtures, or a quantity of any pure olefin compound selected from the ranges specified in this application. The catalysts comprise ferric sulfate supported on alumina or silica-alumina and cobalt sulfate supported on alumina. The weight percent of the iron and the cobalt on the support is in the range of from 0.005% to 50%. The process used in making these catalysts comprises combining ferric sulfate or cobalt sulfate solutions of a minimum 0.05 molar strength with the support desired. In the case of cobalt sulfate, the support is alumina and in the case of ferric sulfate, the support may be alumina or silica-alumina. The support is permitted to adsorb the ferric sulfate or the cobalt sulfate for a period of from 15 minutes to a maximum of 24 hours so that the weight percent of the iron or the cobalt on the support is between 0.005% to 50%. A solid catalyst is then recovered, dried, and calcined. The catalyst should be calcined for a period of time between 1 and 12 hours and at temperatures in the range of 250° C. to 700° C. The iron sulfate on alumina or silicaalumina catalyst and the cobalt sulfate on alumina catalyst is used in a process for the oligomerization of olefins which comprises contacting lightly branched or linear olefins in the range of $C_2$ to $C_{40}$ with the catalyst at temperatures in the range of $-10°$ C. to 400° C. and under pressures between 1 and 75 atmospheres. The oligomerized olefinic product is then collected. Alternative feed stocks may be employed chosen from any olefin in the range of $C_2$ to $C_{20}$ under the same conditions specified for the lightly branched and/or linear olefins in the range of $C_2$ to $C_{40}$.

Some of the desirable qualities which the ferric and cobalt sulfate catalysts of the instant invention provide have been briefly discussed above. These are, specifically, the capability of operation at moderate temperatures, the capability of extreme selectivity for lower oligomers as opposed to higher oligomers, the capability of activity maintenance without water addition, and prolonged activity and avoidance of deactivation from substrate polymerization and coking. Moreover, the instant invention has additional benefits, advantages, and objects which will become apparent to those skilled in this art as this discussion proceeds.

While these catalysts can be prepared by a variety of chemical routes that result in the ferric sulfate or cobalt sulfate affixed to the support, the preferred method of preparation of the catalysts of the instant invention is to combine a solution of ferric sulfate (of a minimum 0.05 molar strength) and a quantity of alumina or silica-alumina support. Alternatively, the catalysts can be prepared by combining a cobalt sulfate solution of a minimum 0.05 molar strength, with alumina support; allowing the support to adsorb the sulfate compound for a period of time preferably between 15 minutes and 24 hours. The solid catalyst is then recovered, rinsed with water, dried and calcined. An acceptable range of calcination temperatures is from 200 to 700 degrees centigrade preferably between 300° and 550° C. The length of time during which the catalyst should be maintained at the calcination temperature depends, among other things, on the necessary removal of water. The catalyst should be maintained at these temperatures during calcination ranging from a minimum of 15 minutes to 24 hours, a preferable time period being from 1 to 7 hours. Acceptable ranges for quantities of iron or cobalt on the support, permit weight percentages as low as 0.005 weight percent and as high as 50 percent. The preferable range for the quantity of iron or cobalt on the support is within the range of about 0.5 to about 25 weight percent.

When these supported ferric sulfate and cobalt sulfate olefin oligomerization catalysts are used, the conditions are acceptable within a variety of ranges. Although any olefin may be employed as a feed in this reaction, a suitable class of olefin for the reaction would be lightly branched and/or linear olefin up to $C_{40}$. An acceptable class of olefin feed would be in the range of $C_2$ to $C_{20}$. The most preferred class of olefin feed, however, is any olefin within the range of $C_3$ to $C_{18}$.

Widely varying conditions of temperature and pressure are also permissible when conducting olefin oligomerization reactions with these catalysts. The pressure used is not critical as long as the pressure selected is sufficient to maintain the reactant olefin in a non-gaseous state where the reaction is taking place. To this extent the pressure will be controlled by the olefin feed which is selected in addition to the temperature. Suitable pressures for olefin oligomerization with this catalyst are within the range of normal atmospheric pressures up to about 75 atmospheres. Preferred pressures are within the range of normal atmospheric pressure up to about 40 atmospheres. The most preferred pressures, however, are from normal atmospheric pressure up to about 30 atmospheres.

Suitable reaction temperatures for these catalysts range from $-10°$ C. to $400°$ C., since for these catalysts, more moderate temperatures are capable of being used. A preferred temperature range is from about $0°$ C. to about $200°$ C. The most preferred range is from $10°$ C. to about $150°$ C. Also, since these catalysts are active at moderate temperatures, it is possible to oligomerize olefins from $C_3$ to $C_{10}$, within an energy conserving range of temperatures from $20°$ C. to $80°$ C. An ideal range for $C_2$ and $C_3$ olefin is $-10°$ C. to $40°$ C.

The oligomerization products are separated and recovered by conventional methods such as fractional distillation, selective extraction, absorption, and processes of this nature. Any reaction diluent used and any unreacted olefin may be recycled.

More specifically, the olefin oligomerization is carried out by contacting the olefin in liquid phase with the surface of the catalyst. While carrying out the oligomerization it may be convenient to use a diluent. Diluent use is not critical. If a diluent is used, the molar ratio of the diluent to the olefin can range up to 10 moles of diluent per mole of olefin. Representative but non-exhaustive examples of suitable diluents are alkanes, such as pentane, hexane, and heptane.

The invention is more concretely described with reference to the examples below wherein all parts and percentages are by weight unless otherwise specified. These examples are provided to illustrate the instant invention and not limit it.

EXAMPLE 1

An 8.75 grams (g) portion of "Catapal®" alumina (Trademark of and sold by Conoco Chemical Co., 1/32" spheres) was soaked in a solution of 2.1 g of hydrated ferric sulfate in 50 milliliters (ml) of water, for a period of 20 hours. The solution was then drained off, and the impregnated alumina was dried overnight at $120°$ C. After drying, the material was calcined for a period of 5 hours at $500°$ C. in air, and was then permitted to cool in a dessicator.

A 5.2 g portion of this catalyst was transferred to a 100 ml autoclave, which was then charged with 20 ml of n-hexane and 28.17 g of cis- and trans-2-butene (Phillips Petroleum Co., Pure Grade). Pressure was put up to 150 pounds per square inch gauge (PSIG) with argon. In the first sample taken during the reaction and analyzed by gas chromatography, after less than 15 minutes of reaction time, while still at $27.9°$ C., it was apparent that butene dimer product was being produced. The contents of the autoclave were stirred magnetically and heated at $65°$ C. for 21 hours. At the end of this interval the catalyst was separated from the product solution by filtration. A 1.0 g sample of the final product solution was combined with 25 milligrams (mg) of a 5% palladium-on-carbon catalyst, and was stirred at room temperature for one hour under 200 PSIG hydrogen pressure to effect the complete hydrogenation of the product olefins. Subsequent analysis of this hydrogenated sample by gas chromatography (methyl silicone stationary phase, in a 50-m (meter) fused silica capillary column) showed a butene conversion of 34%, as calculated by use of the hexane solvent as internal standard. The same analysis showed the butene oligomer to contain 93.5 wt. % dimer, 6.1 wt. % trimer, and 0.4 wt. % tetramer. The hydrogenated dimer was composed of 90.2% by weight 3,4-dimethylhexane, 1.2% by weight 3-methylheptane, and 8.6% by weight other structures.

EXAMPLE 2

A sample of silica-alumina ⅛" pellets (W. R. Grace and Co., Davison Chemical Div., Grade 980-13, 13 wt. % alumina) was ground and sieved to obtain 20-30 mesh granules. An 18.5 g portion of this material was soaked for 20 hours in a solution of 8.04 g of hydrated ferric sulfate in 100 ml of water. The solution was then drained off; the impregnated granules were dried overnight at $120°$ C., and then calcined in air at $485°$ C. for 16 hours.

A 4.2 g portion of this catalyst was placed in a 100 ml autoclave, which was then charged with 20 ml of n-hexane and 24.1 g of cis- and trans-2-butene. Pressure was brought up to about 100 PSIG with argon. The contents of the autoclave were stirred magnetically and heated at $59°$ C. for 10 hours. Subsequent hydrogenation and gas-chromatographic analysis of a product sample as described above showed that the oligomer consisted of 94.0 wt. % dimer, 5.9 wt. % trimer, and 0.1 wt. % tetramer. The composition of the hydrogenated dimer was: 3,4-dimethylhexane, 92.9%; 3-methylheptane, 0.7%; other structures, 6.4%. Conversion of butene was 10.4%.

EXAMPLE 3

A 15 g portion of "Catapal®" alumina (1/32" spheres) was soaked in a solution of 4.55 g of hydrated ferric sulfate in 100 ml of water for a period of 20 hours. The solution was drained off, and the impregnated alumina was dried overnight at $160°$ C. at reduced pressure, then was calcined overnight at $320°$ C. in air.

A 4.1 g portion of this catalyst was placed in a 100 ml autoclave, which was then charged with 20 ml of pentane and 23.7 g of propene. Pressure was then put up to about 75 PSIG with argon. The contents of the autoclave were stirred magnetically and heated at $55°$ C. for 18 hours. Hydrogenation and analysis of a 1.0 g sample of the product mixture as described above showed the oligomer to consist of 19.9 wt. % dimer, 58.8 wt. % trimer, 17.6 wt. % tetramer and 3.7 wt. % pentamer. The hydrogenated dimer was composed of 2,3-dimethylbutane, 92%; 2-methylpentane, 5%; and n-hexane, 3%. Conversion of propene, as determined by the use of the pentane solvent as internal standard, was 41%.

EXAMPLE 4

A mass of 10.02 g of "Catapal®" alumina (1/32" spheres) was soaked in a solution of 5.4 g of cobalt sulfate monohydrate in 100 ml of water for a period of four days. The solution was then drained off and the impregnated alumina was dried overnight at $117°$ C. After drying, the material was calcined for a period of about 5 hours at $500°$ C. under argon, was allowed to cool, and was sealed under argon.

A 1.46 g portion of this catalyst was put into a 100 ml autoclave which was then charged with 20 ml of n-hexane and 30.72 g of cis & trans 2-butene (Phillips Petroleum, Pure Grade). The contents of the autoclave were stirred magnetically, and heated at 33° C. for 21 hours. In the first sample taken during the reaction, and analyzed by gas chromatography, after less than 15 min. of reaction time, while still at 24° C., it was apparent that butene dimer product was being produced. At the end of this interval the catalyst was separated from the product solution by filtration. A 1.0 g sample of the solution was combined with 25 mg of a 5% palladium-on-carbon catalyst, and was stirred at room temperature for one hour under 200 PSIG hydrogen pressure to effect the complete hydrogenation of the product olefins. Subsequent analysis of the hydrogenated sample by gas chromatography (methyl silicone stationary phase, in a 50 m fused silica capillary column) showed a butene conversion of 8.9%, as calculated by use of the hexane solvent as internal standard. The same analysis showed the butene oligomer to contain 94.58 wt. % dimer, 4.45 wt. % trimer, and 0.97 wt. % tetramer. The hydrogenated dimer was composed of 3,4-dimethylhexane, 97.3%; 3-methylheptane, 0.15% and other structures 2.55%.

EXAMPLE 5

A 5.09 g portion of the catalyst prepared as specified in example 4, was put into a 100 ml autoclave, which was then charged with 20 ml of n-pentane and 20.13 g of propene. The contents of the autoclave were stirred magnetically for 18 hours at room temperature. At the end of this interval the catalyst was separated from the product solution by filtration. A 1.0 g sample of the solution was combined with 25 mg of a 5% palladium on carbon catalyst, and was stirred at room temperature for 1 hour under 200 PSIG hydrogen pressure to effect the complete hydrogenation of the product olefins. Subsequent analysis of the hydrogenated sample by gas chromatography (methyl silicone stationary phase, in a 50 m fused silica capillary column) showed a propene conversion of 69% as calculated by use of the pentane solvent as internal standard. The same analysis showed the propene oligomer to contain 19.8% dimer, 43.0% trimer, 26% tetramer, 8.2% pentamer, and 3% hexamer. The hydrogenated dimer was composed of 2,3-dimethylbutene, 83.9%; 2-methylpentane, 1.3%; n-hexane, 14.0%; and other structures 0.8%.

COMPARISON EXAMPLE I

A $NiSO_4/Al_2O_3$ catalyst was prepared by exposing "Catapal®" alumina (1/32" spheres) to an aqueous solution of $NiSO_4$. Thereafter, it was rinsed, dried, and calcined at 500° C. in argon.

The catalyst was then used to oligomerize 2-butene, in a batch reaction system. 5.00 g of the catalyst was put in a 100 ml autoclave with a magnetic stirring bar, 20 ml of hexane, and 25.25 g of 2-butene. The following data was recorded:

| Time | T. °C. | P. psig | Sample # |
|---|---|---|---|
| 10:45 A.M. | 23 | 35 | 1 |
| 11:00 | 42 | 50 | |
| 11:05 | | | |
| 11:15 | 54 | 65 | 2 |
| 11:30 | | | |
| 11:45 | 63 | 80 | 3 |

No product was reflected in Sample #1 or 2.

The reaction was permitted to continue for approximately 57 more hours. Thereafter, a sample of the product was hydrogenated and a subsequent analysis of this sample by gas chromatography (methyl silicone stationary phase in a 50 m. fused silica capillary column) showed the following hydrogenated dimer isomer distribution: 3,4-dimethylhexane, 27.4%; 3,4-methylheptane, 62.4%; octane, 10.2%.

COMPARISON EXAMPLE II

A $NiSO_4/Al_2O_3$ catalyst was prepared by exposing "Catapal®" alumina (1/32" spheres) to an aqueous solution of $NiSO_4$. Thereafter, it was rinsed, dried and calcined at 500° C. in argon. The catalyst was then used to oligomerize 2-butene in a continuous reaction system at a pressure of 500 PSIG and a temperature of 65° C. The following data was recorded:

Total conversion: 38.0%

Hydrogenated dimer distribution: 3,4-dimethylhexane, 28.7% 3-methylheptane, 63.0% Octane, 8.3%

11.0% of the product was trimer.

In view of the available prior art and due to the fact that nickel and iron and cobalt are all of the same family of elements, nickel sulfate supported on alumina was compared to the ferric sulfate and cobalt sulfate catalysts developed in this invention. (See comparison examples). In comparing this nickel sulfate on alumina catalyst to the ferric sulfate and cobalt sulfate catalysts of the instant invention, not only may distinctions be noted, but also advantages of the present catalytic systems over the nickel sulfate on alumina are found. Both the cobalt sulfate and the ferric sulfate catalytic systems exhibit greater activity at lower temperatures than the $NiSO_4$ catalytic system. In addition, the cobalt and iron catalysts both produced less butene trimer than the nickel sulfate system. Thus the catalytic systems of the instant invention are capable of offering greater selectivity toward lower olefin oligomers. The present catalysts and processes also provide a more highly branched product having a better fuel quality than a product which is more linear or less branched. Experimental data indicates that both the cobalt sulfate and the ferric sulfate catalysts produced a highly branched dimer product. Moreover, there is selective production of specific olefin structural isomers within the olefin dimer class. Thus both the cobalt sulfate and ferric sulfate catalytic systems have surprising and unique characteristics which the prior art catalyst ($NiSO_4/Al_2O_3$) was incapable of providing.

While certain details have been shown for the purpose of illustrating this invention, it will be apparent to those skilled in this art that various changes and modifications may be made herein without departing from the spirit or scope of the invention.

Having described our invention, what we desire to secure and claim by Letters Patent is:

1. A process for the oligomerization of olefins which comprises:

contacting lightly branched and/or linear olefins in the range of $C_2$ to $C_{40}$ at temperatures in the range of $-10°$ C. to 400° C., and under pressures between 1 and 75 atmospheres, with a catalyst prepared by combining a ferric sulfate solution of a minimum 0.05 molar strength and alumina or silica-alumina support, permitting the support to adsorb the ferric sulfate for a period between 15 minutes to 24 hours so that the weight percent of iron on the support is between 0.005 to 50%, recovering the solid catalyst, drying and calcining the recovered catalyst for a period of from 1 to 12 hours and at a temperature in the range of 250° C. to 700° C.;

collecting the oligomerized olefinic product.

2. A process for the oligomerization of olefins which comprises:

contacting lightly branched and/or linear olefins in the range of $C_2$ to $C_{40}$ at temperatures in the range of $-10°$ C. to 400° C., and under pressures between 1 and 75 atmospheres, with a catalyst prepared by, combining a cobalt sulfate solution of a minimum 0.05 molar strength and alumina support, permitting the support to adsorb the cobalt sulfate for a period between 15 minutes to 24 hours so that the weight percent of cobalt on the support is between 0.005% to 50%, recovering the solid catalyst, drying and calcining the recovered catalyst for a period of from 1 to 12 hours and at a temperature in the range of 250° C. to 700° C., collecting the oligomerized olefinic product.

3. A process for the oligomerization of olefins as specified in claim 1 wherein the olefins used are in the range of $C_2$ to $C_{20}$.

4. A process for the oligomerization of olefins as specified in claim 3 wherein the temperature range at which the olefin contacts the catalyst is from 0° C. to 200° C.

5. A process for the oligomerization of olefins as specified in claim 4 wherein the olefins used are in the range of $C_3$ to $C_{18}$ and they contact the catalyst at a temperature in the range of from 10° C. to 150° C.

6. A process for the oligomerization of olefins as specified in claim 4 wherein the olefins used are $C_2$ and $C_3$ and they contact the catalyst at a temperature range of from $-10°$ C. to 40° C.

7. A process for the oligomerization of olefins as specified in claim 2 wherein the olefins used are in the range of $C_2$ to $C_{20}$.

8. A process for the oligomerization of olefins as specified in claim 7 wherein the temperature range at which olefin contacts the catalyst is from 0° C. to 200° C.

9. A process for the oligomerization of olefins as specified in claim 8 wherein the olefins used are in the range of $C_3$ to $C_{18}$ and they contact the catalyst at a temperature in the range of from 10° C. to 150° C.

10. A process for the oligomerization of olefins as specified in claim 8 wherein the olefins used are $C_2$ and $C_3$ and they contact the catalyst at a temperature range of from $-10°$ C. to 40° C.

11. A process for the oligomerization of olefins as specified in claim 8 wherein the olefins used are in the range from $C_3$ to $C_{10}$ and they contact the catalyst at a temperature in the range from 20° C. to 80° C.

12. A process for the oligomerization of olefins as specified in claim 4 wherein the olefins used are in a range from $C_3$ to $C_{10}$ and they contact the catalyst at a temperature in the range of from 20° C. to 80° C.

* * * * *